(12) United States Patent
Knebel et al.

(10) Patent No.: US 8,742,163 B2
(45) Date of Patent: Jun. 3, 2014

(54) METHOD FOR PRODUCING METHACRYLATED BENZOPHENONES

(75) Inventors: Joachim Knebel, Alsbach-Haehnlein (DE); Wolfgang Klesse, Mainz (DE); Christine Maria Breiner, Laudenbach (DE); Gerold Schmitt, Aschaffenburg (DE)

(73) Assignee: EVONIK ROEHM GmbH, Darmstadt (DE)

( * ) Notice: Subject to any disclaimer, the term of this patent is extended or adjusted under 35 U.S.C. 154(b) by 555 days.

(21) Appl. No.: 13/122,810

(22) PCT Filed: Nov. 19, 2009

(86) PCT No.: PCT/EP2009/065431
§ 371 (c)(1),
(2), (4) Date: Apr. 6, 2011

(87) PCT Pub. No.: WO2010/072479
PCT Pub. Date: Jul. 1, 2010

(65) Prior Publication Data
US 2011/0196169 A1    Aug. 11, 2011

(30) Foreign Application Priority Data
Dec. 15, 2008   (DE) .......................... 10 2008 054 611

(51) Int. Cl.
*C07C 67/08* (2006.01)
*C07C 69/54* (2006.01)

(52) U.S. Cl.
USPC ........................................................ 560/140

(58) Field of Classification Search
None
See application file for complete search history.

(56) References Cited

U.S. PATENT DOCUMENTS

| | | |
|---|---|---|
| 3,214,492 A | 10/1965 | Tocker |
| 3,265,772 A | 8/1966 | Tocker |
| 3,315,013 A | 4/1967 | Tocker |
| 3,429,852 A | 2/1969 | Skoultchi |
| 4,737,559 A | 4/1988 | Kellen et al. |
| 5,264,526 A | 11/1993 | Kashiwai et al. |
| 2005/0037277 A1 | 2/2005 | Herlihy et al. |
| 2006/0142408 A1 | 6/2006 | Liu et al. |

FOREIGN PATENT DOCUMENTS

| | | |
|---|---|---|
| DE | 1 720 603 | 6/1971 |
| EP | 0 246 848 | 11/1987 |
| EP | 0 346 788 A1 | 12/1989 |
| EP | 0 487 293 | 5/1992 |
| EP | 0 869 138 | 10/1998 |
| EP | 1 676 870 | 7/2006 |
| JP | 2-180909 A | 7/1990 |
| JP | 3-264549 A | 11/1991 |
| JP | 5-112489 A | 5/1993 |
| JP | 2000-191590 A | 7/2000 |
| JP | 2003 261506 | 9/2003 |
| JP | 2003-261506 A | 9/2003 |
| JP | 2007-204448 A | 8/2007 |
| WO | 03 033452 | 4/2003 |

OTHER PUBLICATIONS

International Search Report issued Mar. 19, 2010 in PCT/EP09/65431 filed Nov. 19, 2009.
Osawa, Zenjiro et al. "Preparation of Ultraviolet Stabilizing Polymers. I. Copolymerization of 2-Hydroxy-4-acryloyloxybenzophenone and Its Ultraviolet Stability", Journal of Macromolecular Science: Part A-Chemistry, vol. 1, No. 4, pp. 584-585, XP008119113, ISSN: 0022-233X, (Jul. 1, 1967).
Neidlinger, H.H. et al. "Effect of Polymeric 2-hydroxybenzophenone Stabilizers on the Weathering Of PMMA Films", American Chemical Society, vol. 28, No. 1, pp. 205-206, XP008119138, ISSN: 0032-3934, (Jan. 1, 1987).
Toomey, Ryan et al. "Swelling Behavior of Thin, Surface-Attached Polymer Networks", Macromolecules, vol. 37, No. 3, pp. 882-887, XP002570741, (2004).
Vretik, L. et al. "Polymethacryloylaminoarylmethacrylates: New Concept of Photoalignment Materials for Liquid Crystals", Molecular Crystals and Liquid Crystals, vol. 479, pp. 121/[1159]-134/[1172], XP008095216, ISSN: 1542-1406, (2007).
German Search Report issued on Apr. 4, 2011 in corresponding German Application No. 10 2008 054 611.9 (with an English Translation of Categories).
"Arbeitsvorschrift A", Organikum 17 Aufl. Berlin, VEB Deutscher Verlag der Wissenschaften, 1988, pp. 402-403.
Office Action issued Nov. 11, 2013 in Japanese Patent Application No. 2011-541267 (submitting English translation only).

*Primary Examiner* — Yevegeny Valenrod
(74) *Attorney, Agent, or Firm* — Oblon, Spivak, McClelland, Maier & Neustadt, L.L.P.

(57) ABSTRACT

The invention relates to a method for producing methacrylated benzophenones and to the uses thereof.

6 Claims, No Drawings

METHOD FOR PRODUCING METHACRYLATED BENZOPHENONES

The invention relates to a process for preparing methacrylated benzophenones and to the uses thereof.

Described in the state of the art is a methacrylic anhydride process for preparing the above-stated esters (JP2003261506, Mitsubishi Rayon). Triethylamine is used as catalyst. Since the amine forms a salt with the methacrylic acid produced during the reaction, it must be made equimolar with respect to the benzophenone. Accordingly, equimolar quantities of salt are obtained, which require disposal as waste. Consequently the process is not very economical.

Further methods of the prior art are the reaction of methacryloyl chloride with hydroxy-functional benzophenone, and the reaction of this raw material with glycidyl methacrylate. When using methacryloyl chloride it is necessary to take account of the corrosive and caustic properties. On contact with water, moreover, HCl is released.

DE 1720603 describes a process for preparing aqueous dispersions of readily crosslinkable polymers. In that process, acrylic and methacrylic esters are copolymerized with photoactive, olefinically unsaturated monomers, where appropriate with the accompanying use of photoactive, non-ionogenic emulsifiers.

EP 0346788 describes a process for preparing radiation-sensitive carbamoylbenzo- and -acetophenones having at least one methacrylate or acrylate end group. That process reacts isocyanatoalkyl (meth)acrylates with hydroxyacetophenones or hydroxybenzophenones, using a basic catalyst. It is necessary to operate in the absence of moisture. Moreover, only dried, non-nucleophilic solvents can be used.

The object was to provide an improved process for preparing (meth)acrylic esters of hydroxy-functional benzophenones.

The object has been achieved by a process for preparing benzophenone (meth)acrylates, characterized in that hydroxybenzophenones and (meth)acrylic anhydride are reacted in the presence of catalytic amounts of acid, then the catalyst is neutralized, and subsequently the crude monomer is purified.

The notation "(meth)acrylate" here denotes methacrylate, such as methyl methacrylate, ethyl methacrylate, etc., and acrylate, such as methyl acrylate, ethyl acrylate, etc., and also mixtures of both.

Surprisingly it has been found that, with the process of the invention, high conversions are achieved, and the amount of by-products is greatly reduced. It has been found that the process of the invention is burdened only by a low salt load, which comes about when the catalyst acid is neutralized in the course of work-up. The by-product methacrylic acid can be used as a comonomer in the subsequent polymerization of the benzophenone monomer, or can be recycled for the preparation of new methacrylic anhydride.

The reaction can take place in the presence of common alkylsulphonic or arylsulphonic acids, preferably with sulphuric acid.

Preference is given to reacting 4-hydroxybenzophenone and (meth)acrylic anhydride in the presence of catalytic amounts of concentrated sulphuric acid.

(Meth)acrylic anhydride is added in a slight excess relative to the hydroxybenzophenone. The reaction takes place at temperatures between 50 to 120° C., preferably at 80° C. to 100° C., over 4 to 8 hours, preferably over 5.5 to 6.5 hours.

The catalytically employed acid is neutralized with aqueous bases, preferably with alkali metal hydroxide solution or ammonia solution.

The subsequent work-up of the crude monomer takes place by addition of water. In this way, the impurities are dissolved and can be separated off without problems. The water-soluble impurities of the [(meth)acryloyloxy]benzophenone melt are removed preferably by the addition of water.

[(Meth)acryloyloxy]benzophenone is precipitated by the addition of excess water into the reaction mixture, and is isolated in solid form by filtration.

The benzophenone (meth)acrylates, prepared in high purity, can be stored and reacted further in solution with methyl methacrylate, n-butyl methacrylate, isobutyl methacrylate or styrene.

Benzophenone (meth)acrylates can be used for subsequent photocrosslinking of polymers by daylight or UV light, and also as polymeric photoinitiators.

The benzophenone (meth)acrylates can be used, furthermore, as comonomer for polymerization reactions.

The examples given below are given for better illustration of the present invention, but are not apt to restrict the invention to the features disclosed herein.

EXAMPLES

Example 1

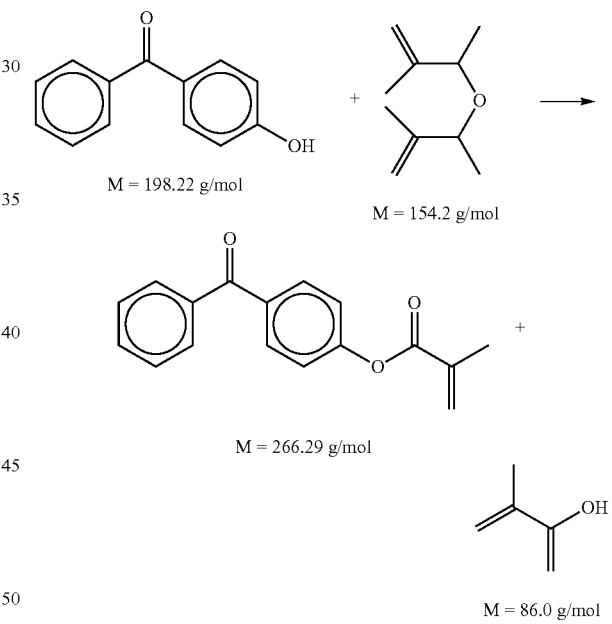

Apparatus: 4 l four-neck round-bottomed flask with mechanical stirrer, reflux condenser, Pt100 temperature sensor, air introduction tube, Anschutz attachment, dropping funnel, electrically heated oil bath Batch:

3.5 mol of 4-hydroxybenzophenone, 99.7%: 695.9 g 3.85 mol of methacrylic anhydride (stabilized with 2000 ppm of 2,4-dimethyl-6-tert-butylphenol): 618.4 g 0.020 mol of concentred sulphuric acid: 1.99 g 1864 mg of hydroquinone monomethyl ether 932 mg of 2,4-dimethyl-6-tert-butylphenol Neutralization of the catalyst acid with 1.8 g of sodium hydroxide in solution in 10 g of water Esterification of the excess methacrylic anhydride with 22.4 g of methanol Theoretical yield: 930.0 g Procedure:

The batch was weighed out completely and then heated to 90° C. with stirring and introduction of air. Reaction time at 90° C.: 6 h. It was then cooled to about 60° C. and the sodium hydroxide in solution in water, for neutralizing the sulphuric acid catalyst, and also the methanol, for esterifying the unreacted methacrylic anhydride, were added. This was followed by stirring at 60° C. for 1 h, after which the batch was poured as thin jet, with stirring (metallic paddle stirrer, stirring motor), into 3 l of water. The mixture was stirred for 0.5 h and the precipitate was then isolated by suction on a glass filter frit, washed with twice 2 l of water, and subsequently subjected to preliminary drying with air on the suction filter. The solid was subsequently dried in air.

Yield: 924.6 g (99.4% of theory)
Analyses: water content: 0.08%
hydroquinone monomethyl ether: 6 ppm
2,4-dimethyl-6-tert-butylphenol: 174 ppm
Gas chromatography:
0.047% methyl methacrylate
0.013% methacrylic acid
0.637% 4-hydroxybenzophenone
97.56% 4-(methacryloyloxy)benzophenone
Pt—Co colour number as 20% strength solution in acetone: 150

Example 2

Apparatus: 4 l four-neck round-bottomed flask with mechanical stirrer, reflux condenser, Pt100 temperature sensor, air introduction tube, Anschütz attachment, dropping funnel, electrically heated oil bath Batch:
1.5 mol of 4-hydroxybenzophenone: 303 g
1.65 mol of methacrylic anhydride (stabilized with 2000 ppm of 2,4-dimethyl-6-tert-butylphenol): 262 g
0.0087 mol of concentred sulphuric acid: 0.84 g
798 mg of hydroquinone monomethyl ether
399 mg of 2,4-dimethyl-6-tert-butylphenol Procedure:

The batch was weighed out completely and then heated to 90° C. with stirring and introduction of air. Reaction time at 90° C.: 6 h. It was then cooled to about 60° C. and the sodium hydroxide in solution in water, for neutralizing the sulphuric acid catalyst, and also the methanol, for esterifying the unreacted methacrylic anhydride, were added. The batch was subsequently stirred at 60° C. for 1 h and then admixed with 1566 g of methyl methacrylate, with stirring. The resulting solution was cooled to room temperature with stirring, and filtered. The solution of the 4-(methacryloyloxy)benzophenone in methyl methacrylate has the following composition as determined by gas chromatography:

56.016% methyl methacrylate
6.954% methacrylic acid
2.399% 4-hydroxybenzophenone
32.717% 4-(methacryloyloxy)benzophenone.

The water content is 0.27%; the stabilizer content is 113 ppm of 2,4-dimethyl-6-tert-butylphenol and 4 ppm of hydroquinone monomethyl ether. The Pt—Co colour number is 169.

The invention claimed is:

1. Process for preparing benzophenone (meth)acrylates, comprising reacting hydroxybenzophenones and (meth)acrylic anhydride in the presence of catalytic amounts of acid, neutralizing said catalyst, and subsequently purifying a crude monomer
   wherein said acid is at least one acid selected from the group consisting of concentrated sulphuric acid, of an alkylsulphonic acid and an arylsulphonic acid.

2. Process according to claim 1, wherein 4-hydroxybenzophenone and (meth)acrylic anhydride are reacted in the presence of catalytic amounts of acid, which are then neutralized with aqueous bases, and subsequently the soluble impurities in a [(meth)acryloyloxy]benzophenone melt are dissolved by addition of water.

3. Process according to claim 1, wherein neutralization is carried out with at least one base selected from the group consisting of aqueous alkali metal hydroxide solution or ammonia solution.

4. Process according to claim 1, wherein said reaction takes place over 4-8 hours at 50 to 120° C.

5. Process according to claim 1, further comprising precipitating a [(meth)acryloyloxy]benzophenone by addition of excess water to the reaction mixture and isolating in solid form by filtration.

6. Process according to claim 1, further comprising adding a liquid (meth)acrylic ester or styrene into the reaction mixture to form a solution.

* * * * *